United States Patent [19]
Kimura et al.

[11] Patent Number: 6,040,495
[45] Date of Patent: Mar. 21, 2000

[54] HAIRLESS MOUSE SENSITIVE TO *HELICOBACTER PYLORI*

[75] Inventors: Nobutake Kimura; Masato Ariga, both of Ohimachi; Hirohito Yamakawa, Nishinasuno-machi; Yoshio Nakagawa; Akio Shimizu, both of Ohimachi, all of Japan

[73] Assignee: Nisshin Flour Milling Co., Ltd., Tokyo, Japan

[21] Appl. No.: 09/047,309

[22] Filed: Mar. 25, 1998

[30] Foreign Application Priority Data

Mar. 25, 1997 [JP] Japan ..................................... 9-071723

[51] Int. Cl.⁷ .................................................... A01K 67/00
[52] U.S. Cl. ...................................................... 800/8; 800/9
[58] Field of Search ............................................. 800/8, 9

[56] References Cited

U.S. PATENT DOCUMENTS 5,602,304 2/1997 Suzuki et al. .............................. 800/8

FOREIGN PATENT DOCUMENTS

WO 96/09757 4/1996 WIPO .

OTHER PUBLICATIONS

Mikio Karita, et al., The American Journal of Gastroenterology, vol. 89, No. 2, pp. 208 to 213, "Establishment of a Small Animal Model for Human *Helicobacter pylori* Infection Using Germ–Free Mouse", 1994.

Jerroid M. Ward, et al., Laboratory Animal Science, vol. 46, No. 1, pp. 15 to 20, "Inflammatory Large Bowel Disease in Immunodeficient Mice Naturally Infected with *Helicobacter hepaticus*", Feb. 1996.

P. Ghiara, et al., vol. 37, No. 01, p. 201, "Infected by *Helicobacter pylori* in a Mouse Model That Mimics Human Disease: Protection by Oral Vaccination", Jul. 7, 1995.

A. A. McColm, et al., vol. 41, No. 1, p. a122, "The Importance of the Challenge Inoculum in Colonisation of HSD/ICR Mice with *H. Pylori*", Sep. 1997.

R. L. Ferrero, et al., vol. 41, No. 1, p. a122, Colonisation of Mice by *H. Pylori* SS1; Similarities with an Acute Infection in Man, Sep. 11, 1997.

Unidentified Curved Bacilli on Gastric Epithelium in Active Chronic Gastritis, The Lancet, Jun. 4, 1983, p. 1273–75.

Yokota K. et al., Colonization of *Helicobacter pylori* in the Gastric Mucosa of Mongolian Gerbils, Microbiol. Immunol. vol. 35(6), 475, 1991.

Marchetti, M., et al., Development of a Mouse Model of *Helicobacter pylori* Infection That Mimics Human Disease, Science, vol. 267, Mar. 17, 1995, 1655–1658.

Smith et al. Clinical and Diagnostic Laboratory Immunology, vol. 3, pp. 66–72, Jan. 1996.

Karita et al. The American Journal of Gastroenterology, vol. 89, pp. 208–213, Feb. 1994.

*Primary Examiner*—Jasemine C. Chambers
*Assistant Examiner*—Deborah J. R. Clark
*Attorney, Agent, or Firm*—Oblon, Spivak, McClelland, Maier & Neustadt, P.C.

[57] ABSTRACT

A hairless mouse designated NS:Hr/ICR is sensitive to *H. pylori*. This NS:Hr/ICR hairless mouse can be easily infected with *H. pylori* in its alimentary canal, and is therefore useful as an experimental animal model for *H. pylori* infection.

6 Claims, No Drawings

HAIRLESS MOUSE SENSITIVE TO *HELICOBACTER PYLORI*

BACKGROUND OF THE INVENTION

1. Field of the Invention

The present invention relates to a hairless mouse designated NS:Hr/ICR which is sensitive to *Helicobacter pylori*. The alimentary canal of the NS:Hr/ICR hairless mouse is infected orally by *H. pylori*. The NS:Hr/ICR hairless mouse is used as an experimental model for *H. pylori* infection.

2. Description of the Related Art

It has been believed for a long time that within the alimentary canal of animals including humans, microorganisms can exist only in the intestine where the pH environment is nearly neutral, and that most microorganisms cannot live in the stomach where the pH environment is acidic and the pH value is 2 or lower. However, the study of the cause and pathology of gastric and duodenal diseases has greatly been changed since J. R. Warren and B. Marshall made it clear in 1983 that *H. pylori*, which is a microaerophilic and spiral Gram negative bacillus, affects gastritis, gastric ulcer and duodenal ulcer (The Lancet, 1273, 1983).

More than ten years have passed since the discovery of *H. pylori* and it is now confirmed that the infection by *H. pylori* in gastric mucosa causes the chronic inflammation of the gastric mucosa, inducing peptic ulcer and leading to gastroduodenal ulcer, and that this chronic inflammation when prolonged leads to atrophic gastritis, further leading to the formation of tumor through the formation of neoplasm on the mucosal epithelium. Moreover, in June, 1994, WHO counseled on the basis of the epidemiological investigation that *H. pylori* is a first class carcinogen.

Under these circumstances, an appropriate animal model is essential for demonstrating that *H. pylori* affects the chronic inflammation of the gastric mucosa, gastroduodenal ulcer and the formation of tumor. With the establishment of an experimental animal model, it would be possible to elucidate the mechanism of the development of diseases by *H. pylori*, such as gastritis, gastric ulcer and duodenal ulcer as well as the formation of tumor through the formation of neoplasm on the mucosal epithelium. Accordingly, many experiments on *H. pylori* infection have been carried out by using animals such as rats, mice, rabbits, dogs, pigs or monkeys. It has been reported that the infection and fixation of *H. pylori* into big animals such as sterilized porcine, sterilized beagle, and monkey were successful but that the infection into small animals such as mice and rats was not easy. Although many experiments on the *H. pylori* infection have been made under various conditions wherein sterilized animals and antibiotics are used, gastric acid is neutralized and the secretion of gastric juice is controlled, no satisfactory result has been obtained.

Recently, it was reported that both nude and euthymic mice were successfully infected with *H. pylori* and that the infection of euthymic mice was only temporary (Karita M. et al, New Small Animal Model for Human Gastric *Helicobacter pylori* Infection: Success in Both Nude and Euthymic Mice, Am. J. of Gastroenterology, Vol. 86, 1596, 1991). It was also reported that Mongolian gerbils were infected successfully by *H. pylori* (Yokota K. et al, Colonization of *Helicobacter pylori* in the Gastric Mucosa of Mongolian Gerbils, Microbiol. Immunol. Vol. 35(6), 475, 1991). The present inventors carried out the same experiment but could not confirm the continued infection of *H. pylori*. Further, Marta Marchetti et al have reported in Science, Vol. 267, Mar. 17, 1995, pages 1655–1658 about the ability of fresh clinical isolates and strains of *H. pylori* to infect specific pathogen-free (SPF)CDI mice, conventional BALB/c and CDI mice.

Under these circumstances, a new small animal model for *H. pylori* infection has been required, which is sensitive to *H. pylori*, easy to breed, easy to orally infect and easy to handle.

SUMMARY OF THE INVENTION

Hairless mice, whose skin is thinner than that of nude mice and similar to that of humans, are often used as an experimental animal for the development of medicine for the prevention or treatment of skin diseases in humans such as skin cancer, skin tumor, bedsores and eczema. The present inventors have also bred hairless mice to be used for the purposes.

Since hairless mice whose genetic characters are identical are needed in order to ensure the reproducibility of the experiments mentioned above, the present inventors mated a male hairless mouse of the ICR strain which was purchased in the market 25 years ago with a female hairless mouse which was also purchased in the market, performed brother-sister mating of the mice generated as the first generation, performed again brother-sister mating of the mice generated as the second generation and repeated this brother-sister mating in 70 generations up to now to acquire an inbred line of hairless mice whose genetic characters are identical, and named them "NS:Hr/ICR hairless mice."

The present inventors have investigated the character of the NS:Hr/ICR hairless mouse and found that *H. pylori* which has difficulty infecting small animals, can easily infect the hairless mouse through an oral route. More specifically, they accomplished this invention by finding that the NS:Hr/ICR hairless mouse is sensitive to *H. pylori* specifically, has a character of being easily infected orally with *H. pylori* without any special means and is useful for an animal model for *H. pylori* infection.

The embryos of the NS:Hr/ICR hairless mouse, an inbred line hairless mouse, was deposited as IAR-NHI 9701 animal on Mar., 19th 1997 at the Institute of Animal Breeding (a foundational juridical person), which is a depository for animals. Embryos of the NS:Hr/ICR hairless were deposited under the terms of the Budapest Treaty on Apr. 3, 1998 at the American Type Culture Collection (ATCC), 10801 University Boulevard, Manassas, Va., 20110-2209, USA, under the ATCC Accession No. 72024. This invention relates to the NS:Hr/ICR hairless mouse whose embryos were deposited as IAR-NHI 9701 at the Institute of Animal Breeding (a foundational juridical person) and, more specifically, it relates to the NS:Hr/ICR hairless mouse which is sensitive to *H. pylori*. This invention also relates to the NS:Hr/ICR hairless mouse whose alimentary canal is orally infected with *H. pylori*, since the NS:Hr/ICR mouse has a special character as an experimental animal model orally infected with *H. pylori* without any special means.

The present invention is directed to a mouse (preferably a hairless mouse), wherein, if the mouse is orally innoculated with a dose of *Helicobacter pylori* (preferably containing from about $1 \times 10^7$ CFU to $2 \times 10^7$ CFU), then there is a probability of greater than 50%, 75%, 95%, or there is a probability of 100% that the alimentary canal (e.g., the gastric mucous membrane) of the mouse will have *Helicobacter pylori* adhered to it one week, four weeks, or eight weeks after the oral innoculation. Advantageously, if the mouse is orally inoculated with two doses of *Helicobacter pylori* (preferably containing from about $1 \times 10^7$ CFU to $2 \times 10^7$ CFU), then there is a probability of greater than 50%, 75%, 95%, or there is a probability of 100% that the alimentary canal (e.g., the gastric mucous membrane) of the mouse will have *Helicobacter pylori* adhered to it one week, four weeks, or eight weeks after the oral innoculation with the second dose. The present invention is also directed to a method for studying the in vivo effect of *Helicobacter pylori* comprising administering *Helicobacter pylori* to the mouse, and studying the in vivo effect of *Helicobacter pylori*.

DETAILED DESCRIPTION OF THE PREFERRED EMBODIMENTS

As mentioned above, the NS:Hr/ICR mouse according to the present invention was obtained by mating a male hairless mouse of the ICR strain which had been purchased in the market 25 years ago with a female hairless mouse which had also been purchased in the market and subsequently subjecting to inbreeding, and has the following morphological characteristics, in addition to the sensitivity to *H. pylori*.

Morphological Characteristics

1) The eyes are red.

2) The skin is of slightly reddish flesh tint until 10 weeks age and thereafter slowly changes to whitish color.

3) The hair comes out on the whole surface of the body 3 or 4 days after birth. The loss of hair starts from the head at 2 weeks age and is completed entirely at 3 weeks age.

4) Change of body weight: The weight of 20 male and 18 female NS:Hr/ICR hairless red several times during a period of 1 to 20 weeks of age to observe the sults are shown in Tables 1 and 2.

TABLE 1

Change of body weight (by gram) for male

| Individual No. | 1 wk | 4 wks | 7 wks | 10 wks | 15 wks | 20 wks |
|---|---|---|---|---|---|---|
| 1 | 4.6 | 14.7 | 25.4 | 29.0 | 30.7 | 30.8 |
| 2 | 4.7 | 15.0 | 26.2 | 29.2 | 31.3 | 31.5 |
| 3 | 4.8 | 15.6 | 26.3 | 30.0 | 32.2 | 32.4 |
| 4 | 4.7 | 16.5 | 27.0 | 27.6 | 28.6 | 28.7 |
| 5 | 4.5 | 15.9 | 27.0 | 28.0 | 29.3 | 29.3 |
| 6 | 4.2 | 15.6 | 26.8 | 28.5 | 30.3 | 30.2 |
| 7 | 4.7 | 14.7 | 26.0 | 29.0 | 30.3 | 30.4 |
| 8 | 4.6 | 13.3 | 25.3 | 29.6 | 30.6 | 30.6 |
| 9 | 4.8 | 12.2 | 22.6 | 25.2 | 26.2 | 26.3 |
| 10 | 4.1 | 11.0 | 21.8 | 25.1 | 25.8 | 25.8 |
| 11 | 4.1 | 9.7 | 20.3 | 24.1 | 24.5 | 24.9 |
| 12 | 4.1 | 9.4 | 20.2 | 23.1 | 23.6 | 23.8 |
| 13 | 3.9 | 12.5 | 24.1 | 25.7 | 26.1 | 26.5 |
| 14 | 3.8 | 14.5 | 26.0 | 26.9 | 28.7 | 28.7 |
| 15 | 4.3 | 16.1 | 26.8 | 29.1 | 30.6 | 30.7 |
| 16 | 4.5 | 16.3 | 27.3 | 30.8 | 31.3 | 31.5 |
| 17 | 3.7 | 14.8 | 26.1 | 27.8 | 28.6 | 28.8 |
| 18 | 4.4 | 14.6 | 25.8 | 28.4 | 28.7 | 28.9 |
| 19 | 4.1 | 13.5 | 24.6 | 26.9 | 27.2 | 27.3 |
| 20 | 4.5 | 16.4 | 28.5 | 31.7 | 32.9 | 31.7 |
| Average Weight | 4.4 | 14.1 | 25.2 | 27.8 | 28.9 | 28.94 |
| Standard Deviation | 0.34 | 2.16 | 3.00 | 2.24 | 2.58 | 2.45 |
| Increase in Average Weight | | 5.1 | 1.4 | 0.9 | 1.1 | 0.04 |

TABLE 2

Change of body weight (by gram) for female

| Individual No. | 1 wk | 4 wks | 7 wks | 10 wks | 15 wks | 20 wks |
|---|---|---|---|---|---|---|
| 1 | 4.2 | 11.7 | 19.9 | 22.0 | 22.0 | 22.1 |
| 2 | 4.8 | 12.4 | 21.6 | 23.1 | 22.8 | 22.7 |
| 3 | 5.0 | 12.3 | 20.4 | 23.3 | 24.1 | 23.9 |

TABLE 2-continued

Change of body weight (by gram) for female

| Individual No. | 1 wk | 4 wks | 7 wks | 10 wks | 15 wks | 20 wks |
|---|---|---|---|---|---|---|
| 4 | 5.3 | 14.1 | 19.2 | 21.1 | 22.0 | 22.3 |
| 5 | 4.5 | 13.9 | 22.4 | 25.0 | 24.6 | 24.8 |
| 6 | 4.5 | 13.9 | 20.4 | 22.9 | 22.9 | 22.7 |
| 7 | 4.4 | 12.7 | 22.7 | 25.8 | 25.3 | 25.5 |
| 8 | 3.9 | 13.4 | 21.8 | 24.0 | 23.9 | 24.1 |
| 9 | 3.6 | 14.4 | 21.7 | 23.8 | 23.7 | 24.1 |
| 10 | 4.5 | 14.7 | 22.8 | 24.5 | 24.7 | 24.5 |
| 11 | 3.7 | 13.4 | 21.8 | 22.9 | 23.2 | 23.8 |
| 12 | 4.6 | 14.4 | 21.3 | 23.8 | 23.8 | 24.0 |
| 13 | 4.2 | 14.5 | 23.0 | 25.7 | 25.8 | 26.1 |
| 14 | 2.8 | 11.4 | 19.5 | 21.9 | 22.9 | 23.0 |
| 15 | 3.6 | 11.9 | 20.1 | 23.4 | 23.6 | 23.4 |
| 16 | 4.1 | 12.2 | 20.6 | 23.8 | 23.9 | 24.1 |
| 17 | 4.6 | 14.2 | 22.4 | 25.4 | 25.7 | 25.9 |
| 18 | 4.6 | 14.6 | 25.5 | 26.5 | 28.1 | 28.3 |
| Average Weight | 4.3 | 13.3 | 21.5 | 23.8 | 24.1 | 24.2 |
| Standard Deviation | 0.59 | 1.12 | 1.54 | 1.46 | 1.50 | 1.54 |
| Increase in Average Weight | | 4.6 | 1.6 | 0.7 | 0.3 | 0.1 | wk(s): week age(s)

5) Biochemical Test: 5 male mice which were 21 weeks of age and 6 female mice which were 23 weeks age were fasted for about 16 hours, and the blood of each mouse was collected from ventral aorta under ether anesthesia, centrifuiged, and the serum was stored at −80° C. and then tested with an autoanalyzer (Hitachi 736/10 type). The results are shown in Table 3.

TABLE 3

Biochemical Test.

Male

| Item/Units | 1 | 2 | 3 | 4 | 5 | Ave. | S.D. |
|---|---|---|---|---|---|---|---|
| TP g/dL | 5.3 | 5.0 | 4.9 | 4.3 | 4.1 | 5.0 | 0.5 |
| ALB g/dL | 1.7 | 1.6 | 1.5 | 1.4 | 1.2 | 1.5 | 0.19 |
| A/G | 0.46 | 0.46 | 0.44 | 0.48 | 0.41 | 0.45 | 0.326 |
| GOT I.U./L | 162 | 150 | 104 | 129 | 137 | 131.4 | 22.1 |
| GPT I.U./L | 65 | 77 | 81 | 27 | 69 | 75.8 | 8.9 |
| ALP I.U./L | 264 | 223 | 183 | 251 | 215 | 227 | 31.2 |
| GLU mg/dL | 17 | 75 | 62 | 43 | 18 | 43 | 25.9 |
| T.GHO mg/dL | 90 | 95 | 76 | 84 | 58 | 80.6 | 14.5 |
| TG mg/dL | 13 | 15 | 31 | 10 | 4 | 14.6 | 10.1 |
| PL mg/dL | 149 | 160 | 149 | 115 | 53 | 125 | 43.8 |
| T.BIL mg/dL | 0.69 | 0.42 | 0.53 | 0.39 | 0.43 | 0.50 | 0.123 |
| BUN mg/dL | 34.7 | 31.2 | 32.6 | 53.0 | 33.9 | 32.1 | 8.99 |
| CRE mg/dL | 0.5 | 0.4 | 0.4 | 0.3 | 0.2 | 0.36 | 0.11 |
| IP mg/dL | 10.1 | 9.8 | 8.8 | 6.9 | 7.0 | 8.5 | 1.51 |
| Ca mEq/L | 4.72 | 4.60 | 4.66 | 4.20 | 4.15 | 4.47 | 0.269 |

Female

| Item/Units | 1 | 2 | 3 | 4 | 5 | 6 | Ave. | S.D. |
|---|---|---|---|---|---|---|---|---|
| TP g/dL | 5.0 | 4.8 | 4.6 | 4.7 | 4.7 | 4.9 | 4.8 | 0.13 |
| ALB g/dL | 1.6 | 1.6 | 1.5 | 1.5 | 1.5 | 1.6 | 1.6 | 0.03 |
| A/G | 0.47 | 0.48 | 0.50 | 0.49 | 0.48 | 0.48 | 0.48 | 0.010 |
| GOT I.U./L | 101 | 95 | 100 | 135 | 71 | 75 | 95 | 22.9 |
| GPT I.U./L | 85 | 60 | 81 | 97 | 65 | 61 | 75 | 15.1 |
| ALP I.U./L | 297 | 269 | 245 | 222 | 209 | 249 | 249 | 31.8 |
| GLU mg/dL | 117 | 110 | 109 | 115 | 102 | 112 | 111 | 5.3 |
| T.GHO mg/dL | 59 | 98 | 91 | 102 | 64 | 82 | 83 | 17.8 |
| TG mg/dL | 84 | 29 | 27 | 25 | 49 | 33 | 41 | 22.7 |
| PL mg/dL | 143 | 190 | 163 | 159 | 127 | 156 | 158 | 21.1 |
| T.BIL mg/dL | 0.93 | 0.39 | 0.27 | 0.34 | 0.46 | 0.39 | 0.46 | 0.237 |
| BUN mg/dL | 41.9 | 33.5 | 27.4 | 33.5 | 41.9 | 38.7 | 36.2 | 5.71 |

TABLE 3-continued

Biochemical Test.

| CRE mg/dL | 0.4 | 0.5 | 0.3 | 0.4 | 0.3 | 0.3 | 0.4 | 0.08 |
| IP mg/dL | 7.2 | 8.0 | 7.1 | 6.8 | 7.3 | 6.9 | 7.2 | 0.43 |
| Ca mEq/L | 4.65 | 5.01 | 4.56 | 4.95 | 4.63 | 4.64 | 4.74 | 0.190 |

Ave.: Average
S.D.: Standard Deviation
In Table 3, the abbreviations of each item in the biochemical test and the test methods thereof are shown below.
TP: Total Protein according to Biuret Method
ALB: Albumin according to BCG Method
A/G: The Ratio of Albumin to Globlin according to ALB/(TP-ALB)
GOT: Aspartic Acid Aminotransferase Activity according to NADH UV-rate assay
GPT: Alanine Aminotransferase Activity according to NADH UV-rate assay
ALP: Alkaline Phosphatase Activity according to p-NPP Method
GLU: Glucose according to GLK-GGPDH Method
T.CHO: Total Cholesterol according to CE-CO-POO Method
TG: Triglyceride according to LPL-GK-GPO-POO Method
PL: Phospholipid according to PLD-COD-POD Method
T.BIL: Total Bilirubin according to Diazo Method
BUN: Urea Nitrogen according to Urease-GLDH Method
CRE: Creatinine according to Jaffe Method
IP: Inorganic Phosphate according to Fiske-Subbarow Method
Ca: Calcium according to OCPC Method 6) Weight of Organs: The animals whose blood had been collected for the biochemical tests were measured for the body weight and the weight of the organs. The results are shown in Table 4.

TABLE 4

Body weight and the weight of organs.

| Actual Weight of Organs (g) | Male | | | | | | |
|---|---|---|---|---|---|---|---|
| | 1 | 2 | 3 | 4 | 5 | Ave. | A.D. |
| Body Weight | 29.47 | 24.00 | 33.09 | 25.27 | 24.58 | 27.28 | 3.89 |
| Brain | 0.485 | 0.429 | 0.475 | 0.499 | 0.425 | 0.463 | 0.034 |
| Heart | 0.241 | 0.153 | 0.229 | 0.160 | 0.162 | 0.189 | 0.042 |
| Lung | 0.202 | 0.159 | 0.220 | 0.175 | 0.184 | 0.188 | 0.023 |
| Kidney (left) | 0.372 | 0.219 | 0.391 | 0.289 | 0.227 | 0.300 | 0.080 |
| Kidney (right) | 0.324 | 0.233 | 0.396 | 0.286 | 0.251 | 0.298 | 0.065 |
| Spleen | 0.159 | 0.060 | 0.069 | 0.059 | 0.059 | 0.081 | 0.044 |
| Liver | 1.378 | 1.072 | 1.726 | 0.912 | 1.045 | 1.227 | 0.327 |
| Testis (left) | 0.119 | 0.105 | 0.109 | 0.109 | 0.100 | 0.108 | 0.007 |
| Testis (right) | 0.120 | 0.107 | 0.111 | 0.108 | 0.102 | 0.110 | 0.007 |
| Thymus | 0.018 | 0.018 | 0.016 | 0.007 | 0.009 | 0.014 | 0.005 |

| Actual Weight of Organs (g) | Female | | | | | | | |
|---|---|---|---|---|---|---|---|---|
| | 1 | 2 | 3 | 4 | 5 | 6 | Ave. | A.D. |
| Body Weight | 27.83 | 27.61 | 25.46 | 24.78 | 24.53 | 23.02 | 25.54 | 1.87 |
| Brain | 0.509 | 0.501 | 0.483 | 0.478 | 0.482 | 0.438 | 0.482 | 0.025 |
| Heart | 0.153 | 0.152 | 0.143 | 0.151 | 0.140 | 0.143 | 0.147 | 0.006 |
| Lung | 0.203 | 0.191 | 0.204 | 0.176 | 0.206 | 0.165 | 0.191 | 0.017 |
| Kidney (left) | 0.248 | 0.240 | 0.222 | 0.217 | 0.232 | 0.211 | 0.228 | 0.014 |
| Kidney (right) | 0.213 | 0.231 | 0.241 | 0.231 | 0.225 | 0.207 | 0.225 | 0.013 |
| Spleen | 0.104 | 0.089 | 0.080 | 0.077 | 0.089 | 0.091 | 0.088 | 0.010 |
| Liver | 1.834 | 1.792 | 1.548 | 1.615 | 1.445 | 1.267 | 1.584 | 0.213 |
| Ovary (left) | 0.008 | 0.008 | 0.006 | 0.005 | 0.006 | 0.007 | 0.0067 | 0.0012 |
| Ovary (right) | 0.007 | 0.007 | 0.006 | 0.005 | 0.005 | 0.006 | 0.006 | 0.009 |
| Thymus | 0.021 | 0.013 | 0.016 | 0.013 | 0.027 | 0.014 | 0.017 | 0.006 |

7) Biochemical marker gene test: The biochemical marker gene test was performed on 6 female hairless mice of 23 weeks of age according to conventional methods. The results are shown in Table 5.

TABLE 5

Biochemical Marker Gene

| Chromosome No. | Locus | Allelic type |
|---|---|---|
| 1 | Idh1 | a |
| 1 | Pep3 | b |
| 1 | Akp1 | b |
| 4 | Mup1 | a |
| 4 | Gpd1 | b |
| 5 | Pgm1 | b |
| 6 | Ldr1 | a |
| 7 | Gpi1 | a |
| 7 | Hbb | d |
| 8 | Es1 | b |
| 8 | Es2 | b |
| 9 | Mod1 | b |
| 9 | Trf | b |
| 11 | Es3 | c |
| 14 | Np1 | a |
| 17 | Glos | a |

The infection of hairless mice with *H. pylori* may be performed by oral administration of (1) a culture solution of *H. pylori* which is cultured separately, (2) a concentrated solution of wet-cells obtained by the centrifugation of the culture solution, or (3) by oral administration with drinking water of the above-mentioned culture solution of *H. pylori* or the prepared solution of wet-cells. Whether the gastric mucosa of a hairless mouse is infected with *H. pylori* is confirmed by killing the hairless mouse, for example, 2 weeks, 4 weeks or 8 weeks after the administration of *H. pylori*, excising the stomach, then washing the contents of the stomach thoroughly, homogenizing the washed stomach tissue, culturing the resulting homogenate on the selective medium for detecting *H. pylori* and identifying a colony if formed. Each wash, after washing the contents of the stomach, was also subjected to cultivation and identification of colonies if any in the same manner as above to confirm the *H. pylori* infection.

*H. pylori* is an aerophil bacterium whose optimum temperature for growth is 37° C. and optimum pH is 6.0 to 8.0. Blood and serum are needed for the growth and it cannot grow on ordinary agar medium. Since various intraorally indigenous bacteria, intestinal bacteria, and Eumycetes are isolated from the gastric mucosa, the culturing method using selective media is usually employed. The slightly aerophil environment for culturing can be easily set up by pouring a medium into a jar of GasPak and generating gas from CampyPak Plus (R). When a smooth, transparent and lustrous colony is observed and weak α-hemolysis is shown after culturing for 3 to 5 days at 37° C., *H. pylori* is putatively identified. By carrying out the bacteriological identification on this colony, the existence of *H. pylori* is confirmed. The selective medium for this bacteria may include BHM (Belo Holizonte Medium), Skirrow medium or Marshall's medium, and commercially available Poremedia HP selective medium (Eiken Kagaku Co. Ltd.) can be also used.

The hairless mouse in which *H. pylori* infection had been established in this way was examined for the existence of *H. pylori* antibody in the serum and the *H. pylori* antibody was confirmed in the serum of the hairless mouse. More specifically, *H. pylori* infection can be confirmed by immobilizing the crude protein fraction of *H. pylori* bacterium (*H. pylori* antigen), adding thereto a diluted mouse serum to be tested, combining a mouse IgG antibody to *H. pylori* in the above mouse serum bound to the *H. pylori* antigen with a labelled anti-mouse IgG antibody prepared separately, and measuring the amount of the labelled anti-mouse IgG antibody according to the ELISA method. Labelling of the anti-mouse IgG antibody used here can be any technique such as enzyme-labelling, fluorescence-labelling and radioisotope-labelling. The animals for which *H. pylori* infection was confirmed can be used in various applications, for example, the establishment of the method of exterminating *H. pylori* by administering drugs such as antibiotics and the establishment of the method of screening of anti-*H. pylori* drugs.

The present invention is illustrated more specifically by referring to the following Examples. However, nothing in these Examples shall be taken as a limitation upon the overall scope of the invention.

EXAMPLES

Example 1

Infection with *H. pylori* (1)

The fresh clinical isolates and strains of *H. pylori* obtained from a university hospital (Strain Reference Number of Nisshin Flour Milling Co., Ltd.: NSP335) was cultured by shaking at 37° C. for three days in BHI (Brain Heart Infusion) with 10% horse serum. This culture was carried out by the GasPack method by using CampyPak Plus. The resultant culture solution of the bacteria was first administered orally at a dose of 1.0 ml per animal (the number of the administered bacteria: $1.1 \times 10^7$ CFU) to male test animals after 48 hours of fasting, whose ages in weeks are listed in Table 1, that is, the hairless mouse in the present invention (NS:Hr/ICR), the hairless mouse put on the market (HOS:HR-1), mice (ICR, DDD, BALB/c and C57BL/6), rats (Wister), and Mongolian gerbils, and 24 hours later 1.0 ml (the number of the administered bacteria: $1.2 \times 10^7$ CFU) of the culture solution of *H. pylori* cultured under the same conditions was administered orally again. At intervals of one and two weeks after the first oral administration, one-half of each of the test animals were killed in order to recover *H. pylori* and assess the stomach tissue.

Whether *H. pylori* adheres to the gastric mucosa was confirmed by washing the contents of the stomach 8 times, homogenizing the stomach tissue, applying the resultant homogenate onto the selective medium for detecting *H. pylori* (Poremedia HP selective medium—Eiken Kagaku Co. Ltd.) and culturing it at 37° C. for 5 days by the GasPak method using CampyPak Plus. The results are shown in the following Table 6.

TABLE 6

| Test Animal | Number of Test Animals | Weeks Age | Number of Infected Animals | |
|---|---|---|---|---|
| | | | 1 wk | 2 wks |
| Hairless mouse (NS:Hr/ICR) | 14 | 7 | 7 | 7 |
| Hairless mouse (HOS:HR-1) | 14 | 8 | 3 | 1 |
| Mouse ICR | 12 | 6 | 1 | 0 |
| DDD | 14 | 7 | 1 | 0 |
| C3H/He | 14 | 8 | 2 | 0 |
| C57BL/6 | 12 | 7 | 0 | 0 |
| BALB/c | 14 | 7 | 2 | 1 |
| Rat (Wister) | 12 | 6 | 0 | 0 |
| Mongolian Gerbil (MON/Jms/Gbs Slc) | 12 | 6 | 0 | 0 | wk(s): week(s)

As shown in Table 6, a complete infection with *H. pylori* was observed in all the hairless mice (NS:Hr/ICR) of the present invention killed after one week of the first oral administration. Similarly, a complete infection with *H. pylori* was observed in all the hairless mice (NS:Hr/ICR) of the present invention killed after two weeks of the first oral administration. On the other hand, the *H. pylori* infection was slightly observed in other test animals killed after one week of the first administration, but hardly observed in other test animals killed after two weeks of the first administration. Separately, each of the three animals which had not been administered the culture solution of *H. pylori* were used as control, and killed at intervals of one and two weeks in the same manner to detect *H. pylori*. All were found to be negative.

Example 2

Infection with *H. pylori* (2)

The three fresh clinical isolates and strains of *H. pylori* obtained from a university hospital (Strain Reference Number of Nisshin Flour Milling Co., Ltd.: NSP335, NSP305 and NSP355) were cultured by the same method as Example 1. The culture solution of bacteria thus obtained was orally administered twice to 15-week-old male hairless mice (NS:Hr/ICR) after 48 hours of fasting in the same manner as Example 1 at a dose shown in Table 7. At intervals of 1, 2, 3 and 4 weeks after the first oral administration, one-fourth of each of the test animals were killed in order to recover *H. pylori* and assess the stomach tissue. The results are shown in Table 7. In this table, "none" in "Bacteria Strain Administrated" column refers to the control animal which was not administered *H. pylori*.

TABLE 7

| Bacteria Strain Admini-stered | Number of Test Animals | Dose | | Number of Infected Animals | | | |
|---|---|---|---|---|---|---|---|
| | | 1st | 2nd | 1 wk | 2 wks | 3 wks | 4 wks |
| none | 12 | — | — | 0 | 0 | 0 | 0 |
| NSP335 | 20 | $1.8 \times 10^7$ | $2.1 \times 10^7$ | 5 | 5 | 5 | 5 |
| NSP305 | 20 | $1.7 \times 10^7$ | $1.9 \times 10^7$ | 5 | 5 | 5 | 5 |
| NSP355 | 20 | $1.4 \times 10^7$ | $2.1 \times 10^7$ | 5 | 5 | 5 | 5 | wk(s): weeks

As clearly shown in Table 7, the establishment of the infection of every fresh strain, which was clinically isolated, into the hairless mouse of the present invention (NS:Hr/ICR), namely 100% infection with fresh clinical isolates and strains of *H. pylori*, was confirmed.

Example 3

Infection with *H. pylori* (3)

The two fresh clinical isolates and strains of *H. pylori* obtained from a university hospital (Strain Reference Number of Nisshin Flour Milling Co., Ltd.: NSP335 and NSP355) were cultured by the same method as Example 1. After culturing, the culture solution of each strain was centrifuged (3,000 rpm, 10 minutes) respectively to prepare a concentrated bacteria solution. Then this concentrated bacteria solution was orally administrated twice to 10-week-old or 11-week-old male hairless mice (NS:Hr/ICR) after 48 hours of fasting in the same manner as Example 1, with the administered number of bacteria (dose) shown in Table 3. At 2 weeks, 4 weeks, 8 weeks after the first oral administration, the animals were killed to examine whether *H. pylori* infection was established. The experimental results are shown in Table 8. In this table, "none" in the "Bacteria Strain Administrated" column means that the control hairless mice were not administered H. pylori.

TABLE 8

| Bacteria Strain Administered | Number of Test Animals | Weeks Age | Dose 1st | Dose 2nd | Number of Infected Animals 2 wks | 4 wks | 8 wks |
|---|---|---|---|---|---|---|---|
| none | 9 | 10 | — | — | 0 | 0 | 0 |
| NSP335 | 15 | 11 | $1.8 \times 10^7$ | $2.1 \times 10^7$ | 5 | 5 | 5 |
| NSP355 | 15 | 10 | $1.4 \times 10^7$ | $2.1 \times 10^7$ | 5 | 5 | 5 | wks: weeks

As clearly shown in Table 8, both strains infected hairless mouse (NS:Hr/ICR) at 100% and the infection continues even 8 weeks later. Moreover, 8 weeks after the administration of the concentrated bacteria solution of H. pylori in the infection experiment as mentioned above, the experimental animals were examined for a viable bacteria number per 100 mg of washed stomach tissues, a histopathological examination and an antibody titer in the serum.

The investigation of the viable bacteria number was carried out by homogenizing the washed stomach tissue again, diluting the resultant homogenate in series, applying them onto the selective medium for detecting H. pylori (Poremedia HP separative medium—Eiken Kagaku Co. Ltd.), culturing them at 37° for 5 days by the GasPak method using CampyPak Plus and calculating the number of appearing colonies in consequence (per 100 mg tissue). The antibody titer in the serum of each experimental animal was determined by ELISA method which comprises immobilizing a crude protein fraction of H. pylori bacterium as antigen onto 96 well microplates, adding a diluted mouse serum thereto and carrying out a colorimetry of a mouse IgG antibody to H. pylori which was bound to the antigen with anti-mouse IgG antibody labelled with peroxidase. The test results are shown in Table 9.

TABLE 9

| Animal No. | Administered Strain | Adhered Bacteria (per 100 mg) | Pathologic Observation Gastritis | Antibody* Titer O.D. (590 nm) |
|---|---|---|---|---|
| 1 | none | — | — | 0.041 |
| 2 | none | — | — | 0.048 |
| 3 | none | — | — | 0.043 |
| 4 | NSP335 | $3.0 \times 10^4$ | + | 0.883 |
| 5 | NSP335 | $4.2 \times 10^4$ | ++ | 0.932 |
| 6 | NSP335 | $2.8 \times 10^4$ | ++ | 1.017 |
| 7 | NSP335 | $1.3 \times 10^4$ | + | 1.102 |
| 8 | NSP335 | $1.6 \times 10^4$ | + | 0.972 |
| 9 | NSP355 | $4.3 \times 10^5$ | ++ | 0.883 |
| 10 | NSP355 | $3.8 \times 10^5$ | + | 0.932 |
| 11 | NSP355 | $1.9 \times 10^5$ | ++ | 1.017 |
| 12 | NSP355 | $2.5 \times 10^5$ | + | 1.102 |
| 13 | NSP355 | $8.7 \times 10^4$ | + | 0.972 |

*Cutoff value: 0.05

The results of the investigation of viable bacteria number, pathologic histology, and the antibody titer in the serum of the experimental animals show that the number of viable bacteria per 100 mg of the stomach tissue which has been washed 8 times is on the order of $10^4$ to $10^5$ and that H. pylori is highly adhered to stomach tissue. The result of the histopathologic examination also shows that inflammatory cells infiltrate into a tunica propria in the gastric mucosa of the infected mouse. Moreover, the measured result of antibody titer show its remarkable increase and it was found that the infection of hairless mouse with H. pylori can be confirmed by the antibody titer examination.

Industrial Applicability

The NS:Hr/ICR hairless mouse of the present invention can be easily infected orally with H. pyloni and can be used as an experimental animal model to elucidate the mechanism of development of the diseases such as gastritis, gastric ulcer and duodeum ulcer as well as the formation of tumor through the formation of neoplasm on the mucousal epithelium and to establish the screening method for the effect of anti H. pylori drugs.

This application is based upon Japanese patent Application No. 9-71723 filed with the Japanese Patent Office on Mar. 25, 1997, the entire contents of which are herein incorporated by reference.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A NS:Hr/ICR hairless mouse whose embryos are deposited with the American Type Culture Collection (ATCC) under accession number ATCC 72024; wherein said mouse is susceptible to Helicobacter pylori infection by oral administration and capable of sustaining Helicobacter pylori alimentary infection, and wherein said mouse is characterized by the following biochemical marker genes:

| Chromosome No. | Locus | Allelic Type |
|---|---|---|
| 1 | Idh1 | a |
| 1 | Pep3 | b |
| 1 | Akp1 | b |
| 4 | Mup1 | a |
| 4 | Gpd1 | b |
| 5 | Pgm1 | b |
| 6 | Ldr1 | a |
| 7 | Gpi1 | a |
| 7 | Hbb | d |
| 8 | Es1 | b |
| 8 | Es2 | b |
| 9 | Modi | b |
| 9 | Trf | b |
| 11 | Bs3 | c |
| 14 | Np1 | a |
| 17 | Glo1 | a. |

2. The hairless mouse of claim 1, which has been infected with Helicobacter pylori for at least one week.

3. The hairless mouse of claim 1, which has been infected with Helicobacter pylori for at least four weeks.

4. The hairless mouse of claim 1, which has been infected with Helicobacter pylori for at least eight weeks.

5. The hairless mouse of claim 1, infected with Helicobacter pylori in its alimentary canal.

6. A method of studying the in vivo effect of Helicobacter pylori comprising administering Helicobacter pylori to a hairless mouse according to claim 1 and assaying for an effect to the mouse.

* * * * *

UNITED STATES PATENT AND TRADEMARK OFFICE
CERTIFICATE OF CORRECTION

PATENT NO. : 6,040,495
DATED : March 21, 2000
INVENTOR(S) : Nobutake Kimura et al.

It is certified that error appears in the above-identified patent and that said Letters Patent is hereby corrected as shown below:

Column 6, Table 5, second column, last entry, "Glos" should read --Glo1--.

Column 10, line 47, second column, "Modi" should read --Mod1--;
　　　　　line 49, second column, "Bs3" should read --Es3--.

Signed and Sealed this

Fifth Day of June, 2001

Attest:

Attesting Officer

NICHOLAS P. GODICI
*Acting Director of the United States Patent and Trademark Office*